United States Patent
Kirn (10) Patent No.: US 9,289,591 B2
(45) Date of Patent: Mar. 22, 2016

(54) JOINT REHABILITATION APPARATUS AND TECHNIQUE

(75) Inventor: Larry J. Kirn, Austin, TX (US)

(73) Assignee: Articulate Labs, Inc., Austin, TX (US)

( * ) Notice: Subject to any disclaimer, the term of this patent is extended or adjusted under 35 U.S.C. 154(b) by 146 days.

(21) Appl. No.: 14/116,005

(22) PCT Filed: May 6, 2012

(86) PCT No.: PCT/US2012/036704
§ 371 (c)(1),
(2), (4) Date: Jan. 31, 2014

(87) PCT Pub. No.: WO2012/154633
PCT Pub. Date: Nov. 15, 2012

(65) Prior Publication Data
US 2014/0148873 A1 May 29, 2014

Related U.S. Application Data

(60) Provisional application No. 61/483,486, filed on May 6, 2011.

(51) Int. Cl.
| | |
|---|---|
| *A61N 1/00* | (2006.01) |
| *A61N 1/04* | (2006.01) |
| *A61N 1/20* | (2006.01) |
| *A61N 1/32* | (2006.01) |
| *A61N 1/36* | (2006.01) |

(52) U.S. Cl.
CPC .............. *A61N 1/0484* (2013.01); *A61N 1/20* (2013.01); *A61N 1/32* (2013.01); *A61N 1/36003* (2013.01)

(58) Field of Classification Search
USPC ............................................. 607/49
See application file for complete search history.

(56) References Cited

U.S. PATENT DOCUMENTS

| | | | |
|---|---|---|---|
| 5,387,231 A | 2/1995 | Sporer | |
| 2003/0028220 A1 | 2/2003 | Piraino et al. | |
| 2007/0203534 A1* | 8/2007 | Tapper | 607/50 |
| 2008/0208287 A1 | 8/2008 | Palermo et al. | |
| 2009/0326602 A1 | 12/2009 | Glukhovsky et al. | |

OTHER PUBLICATIONS

Patent Cooperation Treaty, International Search Report mailed Oct. 4, 2012, for international application No. PCT/ US2012/036704.

* cited by examiner

*Primary Examiner* — Nicole F Lavert
(74) *Attorney, Agent, or Firm* — Trop, Pruner & Hu, P.C.

(57) ABSTRACT

An embodiment includes simultaneously supplying direct current (DC) energy to recondition cartilage of a knee joint while simultaneously protecting that cartilage by supplying alternating current (AC) energy to stimulate muscle tissue contralateral to the cartilage to at least partially decompress the cartilage and at least partially support the joint. Other embodiments are described herein.

18 Claims, 9 Drawing Sheets

JOINT REHABILITATION APPARATUS AND TECHNIQUE

BACKGROUND

Many people experience pain in a joint, such as the knee, elbow, neck, finger, and the like. Much chronic joint pain consists of osteoarthritis characterized by damage to cartilage that protects bone surfaces. Once damaged cartilage regrowth is difficult. Treatment for a damaged joint is limited and may include external bracing, lubricative or anti-inflammatory joint injections, analgesics, or ultimately replacement of the joint with a prosthesis.

Supportive muscle strength and high joint activity may improve long prognoses, yet most of the aforementioned treatment options are inconsistent with the physical activities necessary to retard or prevent disease progression. External bracing, for example, may cause atrophy of the very muscles needed for joint support. Sedation, as another example, discourages high activity. Thus, devices that actively stimulate the body's own musculature surrounding the compromised joint may help rehabilitation. Some such devices are worn throughout the day, constantly monitor the patient's movements, and respond to problematic joint forces by stimulating muscles opposing the incident force causing the problem.

A form of muscle stimulation used in these devices is electrical current. Electrical stimulation that creates a direct current (DC) bias across a muscle, such as galvanic stimulation or unidirectional pulsed waveforms, induces hydrolysis under the electrodes and may cause pain at higher currents. Pure alternation current (AC) (sometimes called symmetric biphasic or polyphasic) waveforms that present no DC component across a muscle may therefore be used for higher stimulation currents. This facilitates maximal contractile effect with less patient discomfort.

In other words, therapy for injured joints still fails to properly balance supporting the joint while fostering rehabilitation of the joint.

BRIEF DESCRIPTION OF THE DRAWINGS

Features and advantages of embodiments of the present invention will become apparent from the appended claims, the following detailed description of one or more example embodiments, and the corresponding figures, in which:

DETAILED DESCRIPTION

In the following description, numerous specific details are set forth but embodiments of the invention may be practiced without these specific details. Well-known circuits, structures and techniques have not been shown in detail to avoid obscuring an understanding of this description. "An embodiment", "various embodiments" and the like indicate embodiment(s) so described may include particular features, structures, or characteristics, but not every embodiment necessarily includes the particular features, structures, or characteristics. Some embodiments may have some, all, or none of the features described for other embodiments. "First", "second", "third" and the like describe a common object and indicate different instances of like objects are being referred to. Such adjectives do not imply objects so described must be in a given sequence, either temporally, spatially, in ranking, or in any other manner. "Connected" may indicate elements are in direct physical or electrical contact with each other and "coupled" may indicate elements co-operate or interact with each other, but they may or may not be in direct physical or electrical contact. Also, while similar or same numbers may be used to designate same or similar parts in different figures, doing so does not mean all figures including similar or same numbers constitute a single or same embodiment.

Bones exhibit piezoelectric properties (e.g., charge that accumulates in materials in response to applied mechanical stress so that electricity results from pressure). Considering bones become stronger in adaptation to stress, and physical stress induces localized currents in the bone, bone growth stimulators sometime apply controlled mechanical stress and/or electrical current to an area. Consistent with observed piezoelectric activity and stress-induced growth of bone and joints, electrical stimulation that imposes a DC bias accelerates tissue regeneration.

Piezoelectric activity is a minor contributor to natural electrical currents in and near joints. Changes in skeletal loading cause fluid flow through bone and particularly cartilage. Due to constituent charged particles, this fluid flow creates dynamic electrical currents which impose streaming potentials across the surrounding tissue. Streaming potentials have significance both from a diagnostic perspective (as measured entities), and in their capacity for fluid flow modulation (as imposed entities). In that flow control of fluids containing charged particles is directly affected by both endogenous and exogenous electrical potentials, impact on cartilage hydration in eroded joints and directed chondrocyte migration (as a likely aid to cartilage regeneration) result from potentials applied to tissue.

Conventional devices that stimulate bone and cartilage growth through electrical stimulation rely on constant excitation or pre-programmed stimulation sequences. In contrast, piezoelectric activity and streaming potentials during normal patient activities are dynamic (e.g., polarities and magnitudes of the currents generated are resultant of incident forces and follow physical activity). Stimulation devices non-responsive to physical activity therefore do not mimic or bolster natural biological piezoelectric or streaming potential activity. Considering synchronizing muscle stimulation with volitional exertion improves both strength and muscle hypertrophy, embodiments of the invention provide improved tissue regeneration based on synchrony between physical stress and stimulation. Pre-programmed stimulation sequences, particularly in view of broad patient-to-patient variances, do not replicate electrical activity resultant of normal activities.

Conventional efforts at cartilage regeneration based on extended application of electrical stimulation are frustrated by destruction of burgeoning growth. Thus, embodiments of the invention protect load-bearing surfaces (during convalescence) from the abuse of daily activities. This is an improvement over prior efforts that protect surfaces via joint disuse for extended periods of time, which are impractical and impair joint function, as well as external mechanical bracing, which necessarily connects to the skeletal system through soft, pliable tissue, that cannot be expected to provide the necessary support. Furthermore, the current provided by these devices is either continuous or follows a pre-programmed sequence. Resultantly, the current delivered cannot possibly approach either the dynamic range or synchrony of piezoelectric currents normally created by the body within healthy joints during normal activities.

Conventional methods concern synchronization of stimulation to the gait cycle for the purpose of impacting cartilage health. Such methods may concern motor-level stimulation of antagonistic muscles in a timed fashion, so as to minimize pressure or moving friction. However, these methods make no distinction between reduced joint forces through antagonistic muscle contraction and charged particle migration through the joint tissue. Stimulation of antagonistic muscles furthermore does not divert force away from compromised load bearing surfaces, as does certain embodiments of the invention that provide stimulation of musculature contralateral to the bearing surface. Unlike such embodiments, the immediately aforementioned conventional method does not concern waveforms applied to both protect the joint and encourage tissue growth.

Other conventional stimulators alter one or more parameters of pre-programmed stimulation patterns in response to body position or inclination, activity level, etc. These devices, however, do not stimulate tissue as a direct function of dynamic physical conditions imposed on the stimulated area such as an embodiment of the invention practices.

Embodiments of the invention include long-term dynamic electrical potentials with modulation of dynamic potentials at very low frequencies holds promise as well.

An embodiment provides ambulant muscle stimulators that may be used to both support compromised joints or skeletal components, and stimulate localized tissue in a manner highly consistent with normal biological activity, both being done with minimal patient discomfort.

Figure 1:
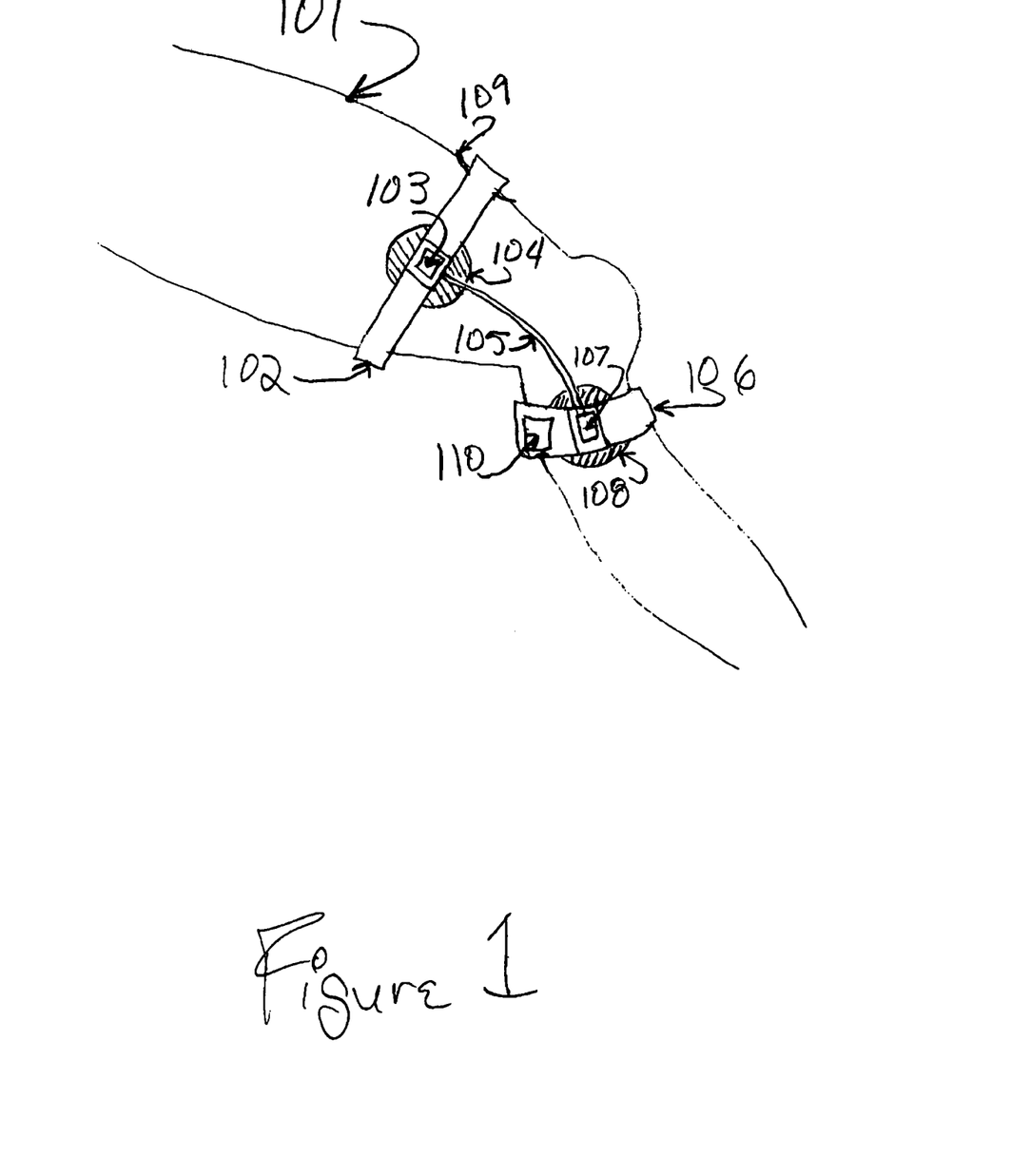
FIG. 1 includes a schematic diagram of a stimulation device in an embodiment of the invention.

FIG. 1 includes an embodiment worn on leg 101. Thigh strap 102 is affixed around the lower thigh of leg 101. Calf strap 106 is affixed around the upper calf of leg 101. Flexible stabilizing member 105 is affixed to straps 102 and 106 and maintains device integrity with relatively constant mean distance between said straps. Although not shown, a similar stabilizing member may be included on the hidden side of leg 101 and may connect straps 102 and 106 to affect symmetrical support. Straps 102 and 106 may consist of one or more materials of any rigidity suitable to maintain relatively constant relative position on leg 101 during active ambulant conditions. Possible examples of straps 102 and 106 construction include thin ABS plastic lined with neoprene, molded silicone rubber, nylon webbing, and/or polypropylene plastic. Stabilizing member 105 may consist of any resilient material, such as nylon, polyethylene and/or acetal. Member 105 may be hollow so as to accommodate wiring between straps 102 and 106.

In an embodiment accelerometers 103 and 107 are affixed to, or integrated within, straps 102 and 106, respectively, to provide both absolute and relative positional and/or motional information. Electrodes 104 and 109 are affixed to the interior surface of strap 102 and electrode 108 is affixed to the interior surface of strap 106. Electrodes 104, 108, and 109 may be composed of electrically-conductive material compatible with human skin, such as stainless steel, conductive rubber, and/or conductive silicone. In an embodiment controller 110 includes signal processing, data processing, and current generation modules (e.g., circuitry and/or software) suitable to stimulate muscle tissue into contraction. Controller 110 receives as input positional and/or motional information from accelerometers 103 and 107, calculates internal vectored forces on at least one internal structural element within the joint, determines appropriate muscle stimulation to be effected as one or more functions of calculated or modeled joint forces, and provides electrical stimulation pulse outputs to at least one electrode, such as electrode 104, 108, or 109. In an embodiment, at least one of electrodes 104, 108, or 109 is presumably located over an area of leg 101 amenable to stimulation of a specific known muscle or muscle group.

In an embodiment, independent motion and accelerations in both sagittal and coronal planes for the femur and tibia of leg 101 are independently provided to controller 110 by accelerometers 103 and 107, respectively, and that stabilizing member 105 serves only to support strap 102 without significantly coupling measurements of the femur and tibia. By the orientation shown, it can be seen that the weight of the embodiment is borne almost entirely by strap 106, which rests upon the superior surface of the gastrocnemius and soleus of Leg 101. In other words, although visually similar to conventional products which brace or support a limb or joint, an embodiment of the device provides virtually or absolutely no physical support to the underlying skeletal structure. In an embodiment protection and/or support of the underlying skeletal structure is affected solely through stimulation of the surrounding musculature. Not only are the surrounding muscles connected to bone far more securely than external bracing (which necessarily operates through soft tissue), muscular strength is improved through stimulated use, rather than atrophied through the enforced disuse of external bracing.

Figure 2:
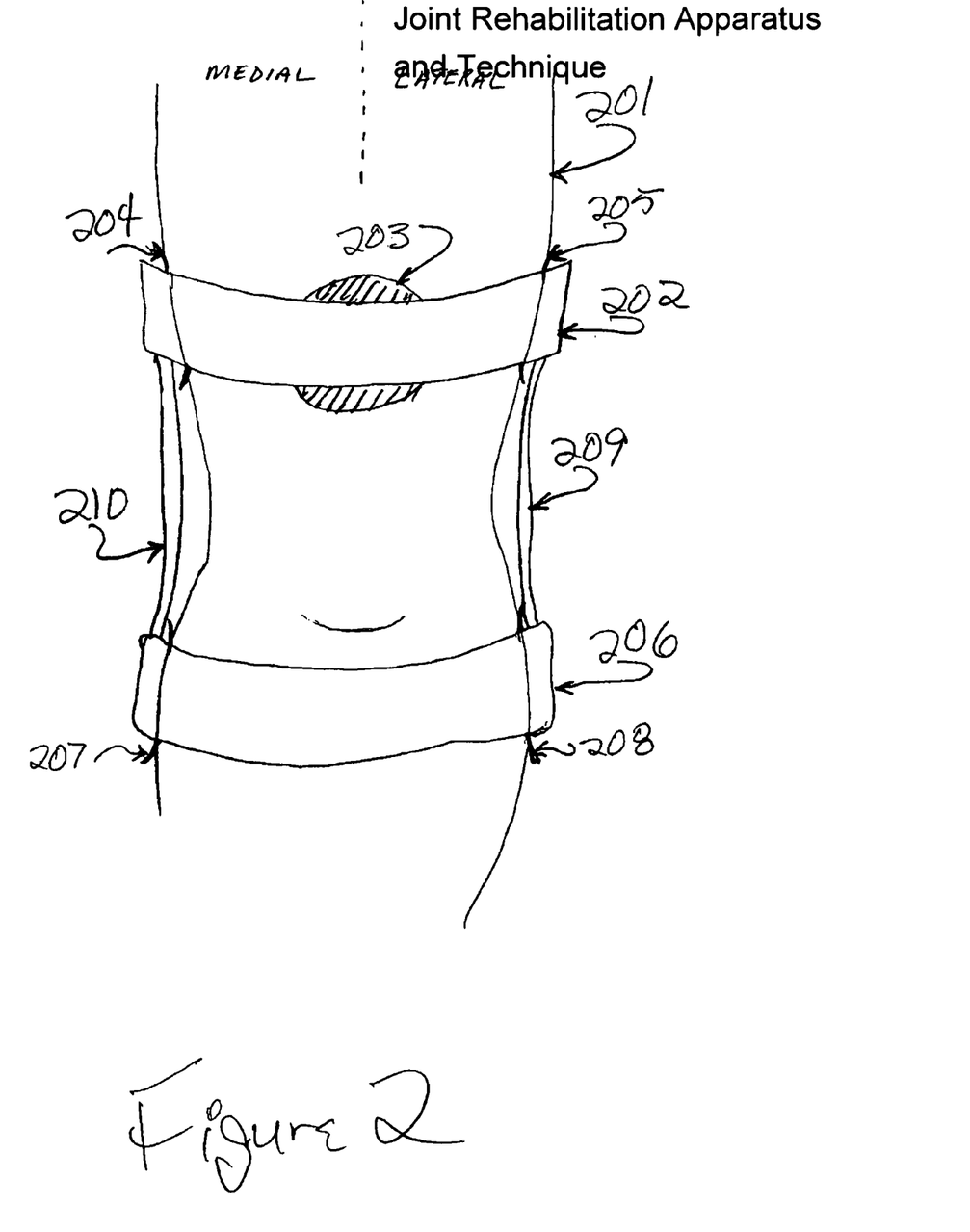
FIG. 2 includes a schematic diagram of a stimulation device in an embodiment of the invention.

Referring now to FIG. 2, an anterior view of an embodiment is shown being worn on leg 201. Thigh strap 202 is being affixed around the lower thigh of leg 201, calf strap 206 is affixed around the upper calf of leg 201, and flexible stabilizing members 209 and 210 which, being affixed to both straps 202 and 206, maintain device integrity with relatively constant mean distance between said straps. Electrodes 203, 204, and 205 are affixed to the interior surface of strap 202 and electrodes 207 and 208 are affixed to the interior surface of Strap 206. Position and number of electrodes shown in FIG. 2 are for illustrative purposes only and alternative configurations are within the scope of an embodiment of the invention.

Leg 201 is illustrated as a human left leg. Electrodes 204 and 203, when differentially driven, are positioned to provide stimulation current across the medial vastus, and electrodes 205 and 203 are positioned to provide stimulation current across the lateral vastus. Current through one or both condyles of the knee may be provided at various angles by differential driving of electrodes 204, 203, and/or 205 in conjunction with electrodes 207 and/or 208.

Figure 3A:
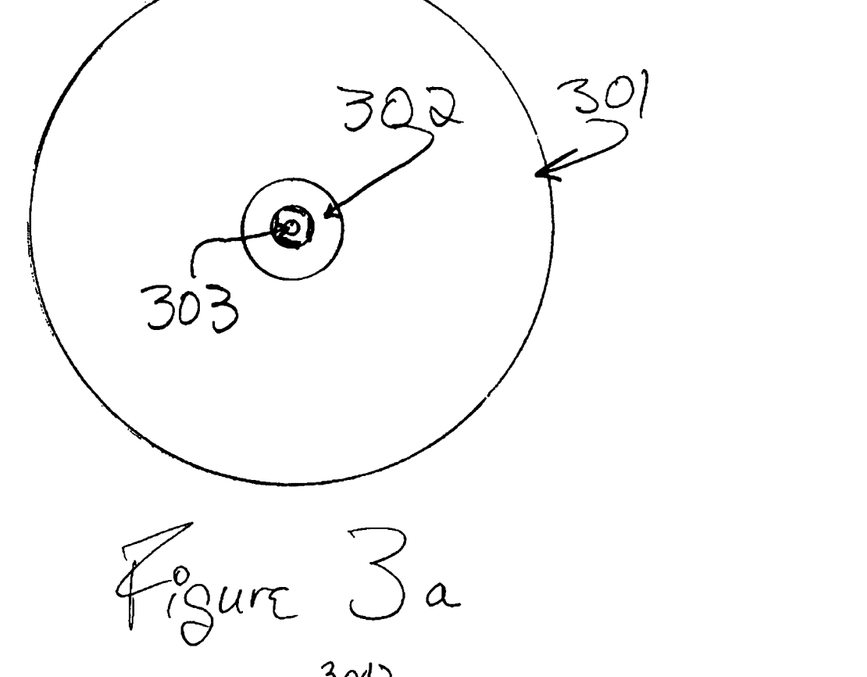
FIGS. 3a-b include schematic diagrams of an electrode in an embodiment of the invention.

In FIG. 3a pivot Seat 302 is coupled to electrode face 301. Electrode face 301 includes an electrically-conductive material suitable for long-term contact with human skin, such as stainless steel. Alternatively, electrode face 301 may be a lamination of materials, or any other material suitable to transfer electrical energy through human skin. The side of electrode face 301 that is presented to skin may be processed so as to provide maximum surface area to the skin. In the case of stainless steel, this may be accomplished by sandblasting the surface with sharp media. In the case of conductive elastomers this may be accomplished through molding this surface with a non-smooth texture. Pivot seat 302 may include any material that may readily be attached to electrode face 301, and may be electrically conductive (e.g., brass or titanium) or non-conductive. In the latter case, alternative means to couple electrical current to electrode face 301 may be used. Pivot 303 inserts into pivot seat 302 and is preferably retained therein, such as through post-insertion crimping of pivot seat 302. Pivot 303 may also be comprised of a conductive material, such as brass or titanium, or any other robust material if alternative means to couple current into electrode face 301 are used. Retention of pivot 303 within pivot seat 302 is loose enough to allow swiveling motion of pivot 303 within pivot seat 302, while yet preventing full release of pivot 303.

Figure 3B:
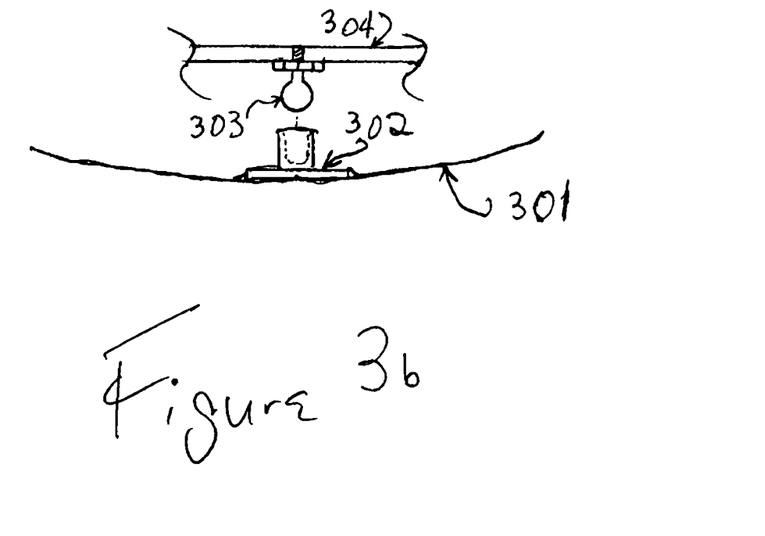

In FIG. 3b pivot seat 302 is firmly attached to electrode face 301 through means such as soldering, brazing, spot welding, or any other mechanical fixation suitable for the materials used. Pivot 303 inserts into, and is to be retained by, pivot 303 as noted in FIG. 3a above. Pivot 303 is mechanically attached to strap 304, shown abbreviated. Full depiction of strap 304 may be seen in FIG. 1 as strap 102 or strap 106. If, for example, pivot seat 402 comprises brass or titanium, pivot 303 may also comprise brass, titanium, or any other such robust material. Strap 304 may include integrated or non-integrated means to provide individual electrical coupling ultimately between controller 110 of FIG. 1 and each electrode shown in FIG. 1 and/or FIG. 2.

Figure 4:
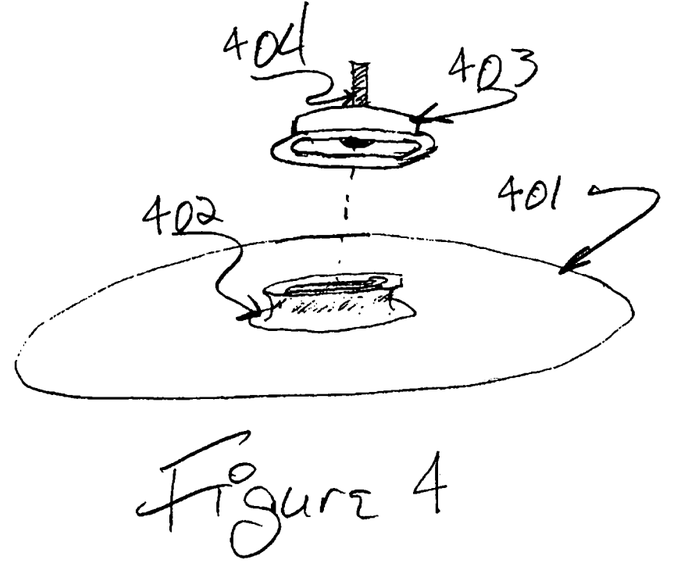
FIG. 4 includes a schematic diagram of an electrode in an embodiment of the invention.

In FIG. 4, male Snap Fastener 402 is rigidly secured to electrode 401. Electrode 401 may be of any material suitable to impart electrical current through the skin, such as stainless steel or titanium. In this case, fastener 402 may be attached to electrode 401 by brazing, spot welding, soldering, or any other method known in the art. Alternatively, electrode 401 may consist of one or more rigid non-conductive substrates laminated with conductive material suitable for charge transfer. In this case, fastener 402 may be attached to electrode 401 using conductive adhesive, such as epoxy, captive clamping, or any other method to ensure electrical connectivity.

In an embodiment male snap fastener 402 inserts into female snap fastener 403, which is attached to or through strap 102 or 106 of FIG. 1. Attachment means for fastener 403 are to provide electrical conductivity, such as that through metallic screw 404, to connective means within or upon strap 102 or 106 to appropriate output switches within controller 110, all of FIG. 1. In the event that strap 102 or 106 is not self-supportive, a backing plate behind or within the strap may be used to provide robust mechanical and electrical connection.

The degree to which Electrode 401 may pivot upon fastener 403 may be easily controlled by relative sizes of fasteners 402 and 403, or through tension of an internal ring spring within fastener 903.

The foregoing discussion of FIGS. 3a-b and 4 describes embodiments of rigid structures that conform to movement of underlying tissue, hence providing maximal electrode contact with underlying skin through physically dynamic circumstances. Alternative implementations, such as spring-retained snap fasteners, are included in embodiments. The pivoting electrode suspension embodiments provide integral electrode connection with no central electrode compliance, hence coupling electrode pressure directly to that of the supporting strap. Furthermore, an embodiment provides no intrinsic mechanical support of the joint but relies solely upon the surrounding musculature for joint protection. Being directly coupled to the skeletal system, surrounding musculature provides far better support than any system which must perform this function through soft tissue.

By the discussion above, it can be seen that electrical muscle stimulation signals may be individually coupled from controller 110 of FIG. 1 to electrodes 203, 204, 205, 207, and 208, all of FIG. 2. The central pivot of various embodiments allows each of said electrodes to individually self-adjust to the optimal planar position which presents maximum skin contact when straps 102 and 106 of FIG. 1 are pressed against Leg 101. In an embodiment, two pivots per electrode are used to provide/restrict movement in a single axis.

In FIG. 2 leg 201 the left leg of a person. Resultantly, the side of leg 201 on which support 210 resides is the medial leg surface. The effect of adduction moment on leg 201 as it is loaded, therefore, causes central knee motion laterally. That is, the distal femur and proximal tibia both move laterally. The effect of this motion compresses the medial capsule within medial side of the knee as shown. The waveforms of FIG. 5 show operation of an embodiment of the invention in this situation of medial condyle compression or collapse.

Figure 5:
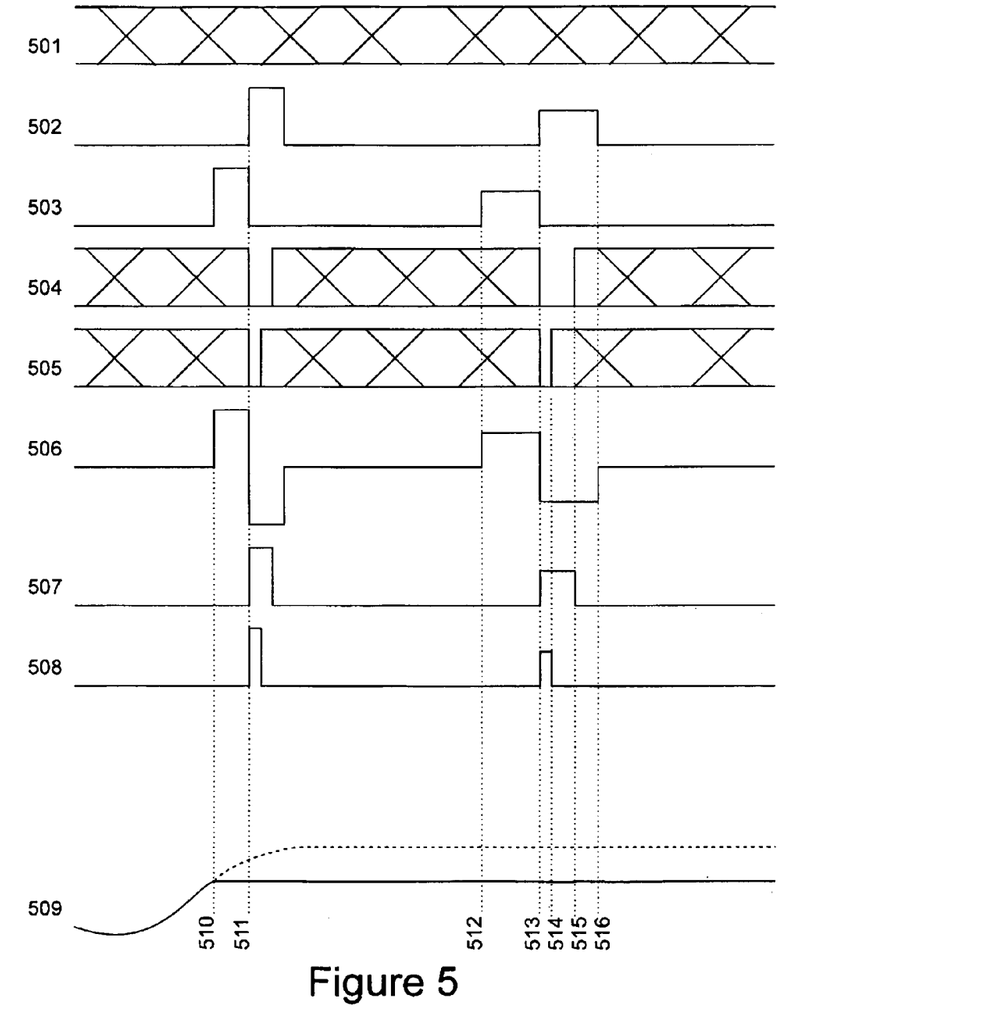
FIG. 5 includes a stimulation regimen in an embodiment of the invention.

Referring now to FIG. 5, waveforms 501, 502, 503, 504, and 505 show stimulation current as applied to electrodes 204, 203, 205, 207, and 208, respectively, all of FIG. 2. Waveforms 506, 507, and 508 show resultant differential currents between electrodes 205 and 203, electrodes 203 and 207, and electrodes 203 and 208, respectively. Periods of time in which high impedance is presented to an electrode are denoted by cross-hatching. Correlating back to FIG. 2, waveform 506 therefore shows differential current (AC energy) applied across the lateral vastus of leg 201; waveform 507 shows differential current (DC energy) applied from the center of the femur through the medial condyle of the knee; and waveform 508 shows differential current (DC energy) applied from the center of the femur through the lateral condyle of the knee.

Waveform 509 shows compressive force incident upon the medial condyle of the knee, deflection upward denoting increasing force. The dotted extension of waveform 509 shows compressive force that would occur in the absence of muscle stimulation provided by the current invention. Force depicted in waveform 509 is presumably calculated by controller 110 of FIG. 1, using a software model of the physical knee responsive to outputs of accelerometers 103 and 107, also of FIG. 1. The X (horizontal) axis of FIG. 5 represents time, during which leg 101 of FIG. 1 enters a stance phase.

Waveform 501, representative of current supplied to electrode 204 of FIG. 2, remains in a high-impedance state. In the example shown of medial capsule force compensation, medial counter-force is not required. In contrast to prior practice, electrode 204 of FIG. 2 remains in an agnostic state preventing diversion of any current from either electrode 203 or 205.

At the left side of FIG. 5, medial capsule force 506 is at zero, presumably as leg 101 of FIG. 1 ends swing phase. Proceeding to marker 510, force 509 has increased to a level indicating need of compensatory action. Presumably this increased force is caused by loading the leg upon entering stance phase in a fashion so as to create excessive force on the medial capsule. In response to the higher medial force indicated at marker 510, controller 110 of FIG. 1 begins muscle stimulation of the vastus lateralis. This muscle stimulation is effected by initial issuance of a current pulse to electrode 205 of FIG. 2, shown in waveform 503, followed by a current pulse to electrode 203 of FIG. 2, shown at marker 511 in waveform 502. The issuance of two unipolar currents across a muscle area in this fashion essentially creates a bipolar differential current, as shown in waveform 506. This technique is prevalent in switching output stage designs, to provide bipolar output capability from a single supply source.

Continuing to the right through FIG. 5, waveforms 502 and 503 remain at zero current until marker 512, at which point current is sourced into electrode 205 of FIG. 2, as shown in waveform 503. Note that the magnitude of this current, shown by its height, is less than the earlier waveform 503 pulse, but that its width, to marker 513, is longer. The charge applied by the waveform 503 pulses at markers 510 and 512 are therefore roughly equivalent, but the voltages for any given load impedance are vastly different. Patient comfort and uniform contractions through wide impedance variations are accommodated through converse modification of stimulation pulse current and width. Note that this converse modification is adjusted independently from adjustment of the amount of charge to be delivered to musculature for any given set of conditions. At marker 513 cessation of the pulse to electrode 205 and initiation of a pulse to electrode 203, both of FIG. 2, is seen in waveforms 503 and 502, respectively. Resultant differential current across the lateral vastus is again seen between markers 512 and 516 in waveform 506.

Note in waveforms 504 and 505 that electrodes 207 and 208 of FIG. 2 briefly sink current during the periods in which waveform 502 indicates sourced current to electrode 203 of FIG. 2. Specific timing of this activity is seen at marker 513, wherein waveforms 504 and 505 both indicate current sinking at the onset of current sourcing in waveform 502. This condition continues until marker 514, at which point waveform 505 reverts to a high impedance state. Continuing further, waveform 504 returns to a high impedance state at marker 515, which is substantially before cessation of waveform 502 current sourcing at marker 516. In that waveforms 504 and 505 indicate current applied to electrodes 207 and 208, respectively, the net effect of waveform 504 and 505 activity just described serves to induce a small pulsed direct current seen in waveform 508 through the lateral side of the knee, and a somewhat larger pulsed direct current seen in waveform 507 through the medial side of the knee. The purpose of this direct current is to encourage cartilage regeneration (which can accomplish many benefits include reduced pain, reduced "night pain", and the like). To this end, higher pulsed current is directed through the portion of the joint being mechanically protected by muscle contraction. That is, stimulation of lateral muscle is accompanied by larger medial direct current, and conversely, stimulation of medial muscle is accompanied by larger lateral direct current. Furthermore, note that direct current may be applied through the joint while symmetrical alternating current, with no DC component, is applied to nearby musculature. Variances in relative and absolute timing of this operating principal are anticipated.

Figure 6:
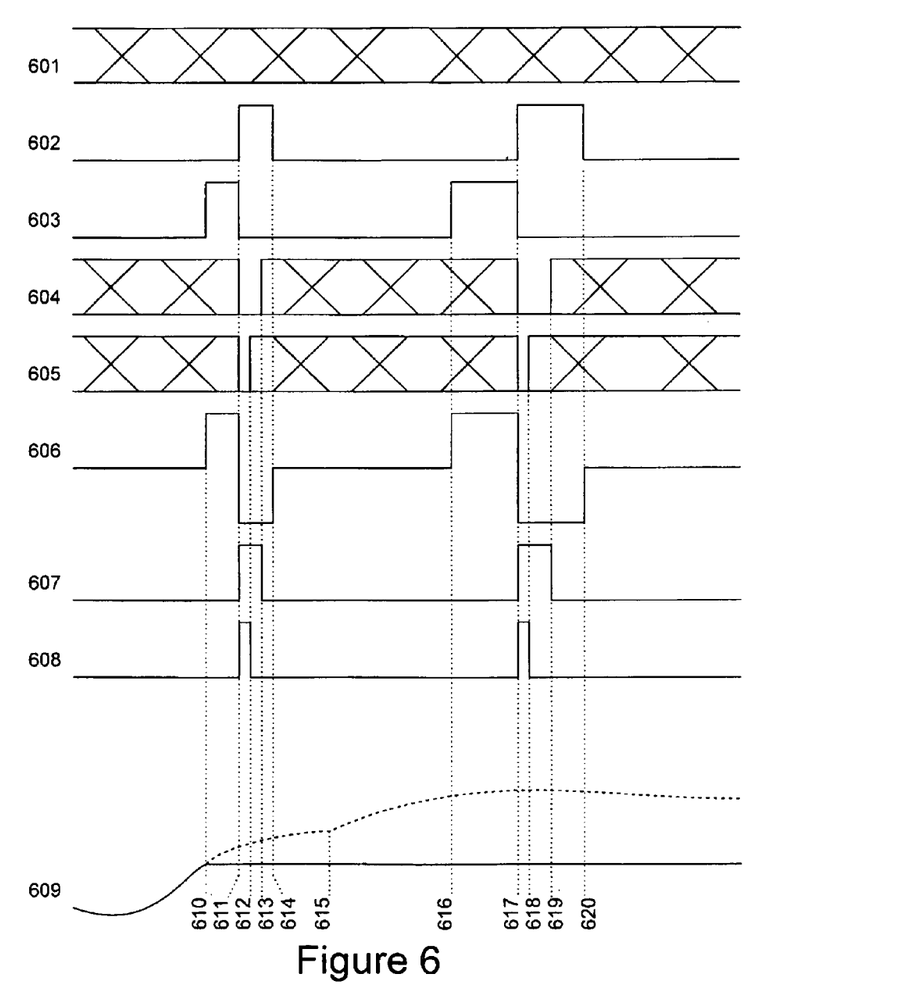
FIG. 6 includes a stimulation regimen in an embodiment of the invention.

In FIG. 6 waveforms 601, 602, 603, 604, and 605 show stimulation current as applied to electrodes 204, 203, 205, 207, and 208, respectively, all of FIG. 2. Waveforms 606, 607, and 608 show resultant differential currents between electrodes 205 and 203, electrodes 203 and 207, and electrodes 203 and 208, respectively. Periods of time in which high impedance is presented to an electrode are denoted by crosshatching. Correlating back to FIG. 2, waveform 606 therefore shows differential current (AC energy) applied across the lateral vastus of leg 201; waveform 607 shows differential current (DC energy) applied from the center of the femur through the medial condyle of the knee; and waveform 608 shows differential current (DC energy) applied from the center of the femur through the lateral condyle of the knee.

Waveform 609 shows compressive force incident upon the medial condyle of the knee, deflection upward denoting increasing force. The dotted extension of waveform 609 shows compressive force that would occur in the absence of muscle stimulation provided by the current invention. Force depicted in waveform 609 is again presumably calculated by controller 110 of FIG. 1, using a software model of the physical knee responsive to outputs of accelerometers 103 and 107, also of FIG. 1. The X (horizontal) axis of FIG. 6 represents time, during which leg 101 of FIG. 1 enters stance phase.

Waveform 601, representative of current supplied to electrode 204 of FIG. 2, again remains in a high-impedance state. In the example shown of medial capsule force compensation, medial counter-force is not required. In contrast to prior practice, electrode 204 of FIG. 2 remains in an agnostic state, preventing diversion of any current from either electrode 203 or 204.

At the left side of FIG. 6, medial capsule force 606 is at zero, presumably as leg 101 of FIG. 1 ends swing phase. Proceeding to marker 610, force 609 has increased to a level indicating need of compensatory action. Presumably this increased force is caused by loading the leg upon entering stance phase in a fashion so as to create excessive force on the medial capsule. In response to the higher medial force indicated at marker 610, controller 110 of FIG. 1 begins muscle stimulation of the vastus lateralis. This muscle stimulation is effected by initial issuance of a current pulse to electrode 205 of FIG. 2, shown in waveform 603, followed by a current pulse to electrode 203 of FIG. 2, shown at marker 611 in waveform 602. The resultant bipolar current between markers 610 and 614 across the vastus lateralis is shown in waveform 606. Following the example of FIG. 5, electrode 207 of FIG. 2 sinks current from electrode 203 between markers 611 and 613, as shown in waveforms 604 and 607; and electrode 208 of FIG. 2 sinks current from electrode 203 between markers 611 and 612, as shown in waveform 605 and 608. Of course in other embodiments the sinking periods may be equal or flip-flopped to manipulate DC energy applications.

Continuing to the right through FIG. 6, medial condyle force, shown in waveform 609, again increases at marker 615. At marker 616, a longer current pulse is initiated to electrode 205 of FIG. 2, as shown in waveform 603, followed at marker 617 by a current pulse to electrode 203 of FIG. 2, as shown in waveform 602, which terminates at marker 620. The resultant bipolar current applied across the vastus lateralis is again shown in waveform 606. The increase in waveform 606 pulse width shows immediate response to the force increase indicated in waveform 609 at marker 615.

As electrode 203 of FIG. 2 begins to source current, shown in waveform 602 at marker 617, electrodes 207 and 208 of FIG. 2 again begin to sink current, as shown in waveforms 604 and 605, respectively. (In other embodiments sinking may occur during pulses of signal 603 instead of or in addition to pulses of signal 602.)

Current sinking into electrode 208 of FIG. 2 continues to marker 618, shown in waveform 605. Note that the resultant current pulse widths to electrode 208 of FIG. 2, shown in waveform 608 remain constant, between markers 611 and 612; and markers 617 and 618. DC current applied to electrode 208 of FIG. 2 is therefore constant, in spite of the increase of AC current shown in waveform 606 between markers 616 and 620.

Current sinking into electrode 207 of FIG. 2 continues to marker 619, shown in waveform 604. Note that the resultant current pulse width to electrode 207 of FIG. 2, shown in waveform 608 between markers 617 and 619 is longer than the preceding electrode 207 pulse between markers 611 and 613, but that the width increase between markers 617 and 619 is disproportionately shorter than the increase in AC stimulation pulse width from markers 610 to 614 and markers 616 to 620 shown in waveform 606. This again shows independence between AC and DC stimulation, both entities yet being controlled as a function of force indicated in waveform 609.

Note that the stimulation pulses shown in waveforms 601, 602, 603, 604, and 605 are output at a constant rate, the period of which is seen between markers 611 and 617. Specifically, the period between sign reversals of AC output currents (rather than initiations of the first current pulse) remains constant via implementation of a "centered PWM" (pulse width modulation) technique. The center of integrated output current from each bipolar pulse is therefore equidistant, obviating instantaneous phase disturbances that would otherwise be imposed by integral center movement from pulse width variances. This technique does not obviate use of imbalanced sink and source pulse widths with the current invention. Unbalanced sink and source pulse widths or currents may be included in various embodiments to address independent control of DC and AC components when both are required across an electrode pair.

Figure 7:
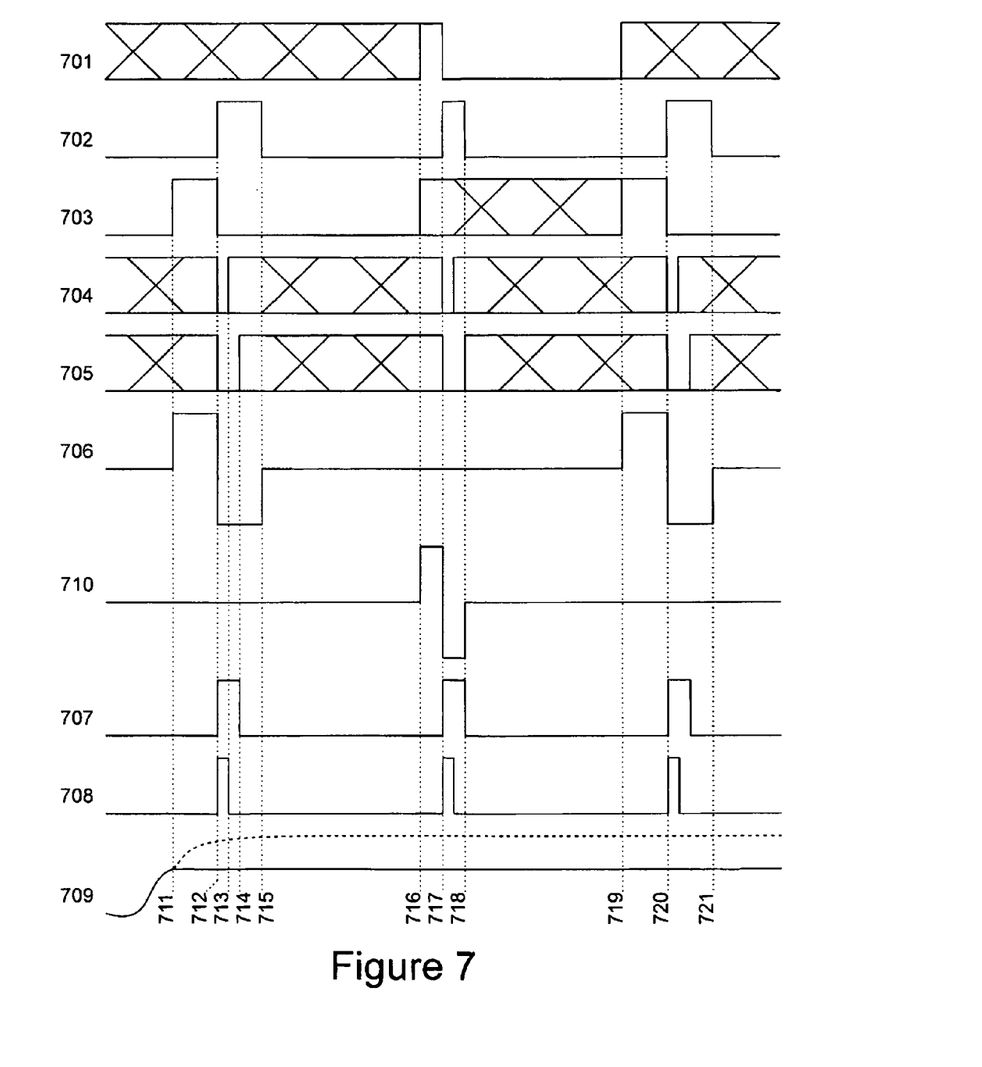
FIG. 7 includes a stimulation regimen in an embodiment of the invention.

In FIG. 7 waveforms 701, 702, 703, 704, and 705 show stimulation current as applied to electrodes 204, 203, 205, 207, and 208, respectively, all of FIG. 2. Waveforms 706 (AC energy), 707 (DC energy), 708 (DC energy), and 709 show resultant differential currents between electrodes 205 and 203, electrodes 204 and 203, electrodes 203 and 207, and electrodes 203 and 208, respectively. Periods of time in which a high impedance is presented to an electrode are denoted by cross-hatching. Waveform 710 (AC energy) shows posterior force incident within the knee upon the tibia relative to the femur, a force which is typically problematic after a rupture of the posterior cruciate ligament. Deflection upward denotes increasing proximal tibial force. The dotted extension of waveform 710 shows relative force between the tibia and femur that would occur in the absence of muscle stimulation provided by the current invention. Relative force depicted in waveform 710 is presumably calculated by controller 110 of FIG. 1, from information received from accelerometers 103 and 107, also of FIG. 1. The X (horizontal) axis of FIG. 7 represents time as leg 101 of FIG. 1 enters stance phase.

At marker 711 waveform 710 shows adequate tibia-femur knee force to approach potentially damaging posterior-anterior knee misalignment under load. In response to this detected condition, controller 110 of FIG. 1 begins output of alternating muscle stimulation pulses to constrain internal knee forces within safe boundaries, the first current pulse being directed to electrode 205 of FIG. 2, as seen in waveform 703. At marker 712 electrode 204 of FIG. 2 is caused to sink current, and current sourcing commences at electrode 203 of FIG. 2, as shown in waveforms 703 and 702. A bipolar current pulse is therefore applied to the lateral quadriceps muscle of the upper leg, as seen in waveform 706 (AC energy), inducing contraction of the lateral vastus. Following an inter-pulse delay period, current sourcing into electrode 204 of FIG. 2 occurs between markers 716 and 717, after which electrode 204 of FIG. 2 sinking occurs while current is sourced again into electrode 203 of FIG. 2, until marker 718. An inter-pulse again is imposed until marker 719. A bipolar current pulse is therefore applied to the medial muscle of the upper leg, as seen in waveform 707 (DC energy). The charge applied to the lateral muscle between markers 711 and 715 is visibly larger than the charge applied to the medial muscle between markers 716 and 718, creating a differential in the contractile force induced. Note also that use of electrode 203 of FIG. 2 is shared between lateral muscle stimulation, medial muscle stimulation, lateral pulsed joint current, and medial pulsed joint current. Similar shared use of any electrode in an embodiment of the present invention is anticipated.

Quasi-simultaneous stimulation of both lateral and medial muscles increases the amount of tensile force induced. Differential of stimulation charge between lateral and medial sides may be statically or dynamically determined by controller 110, based on factors such as knee conditions indicated by a health provider, knee conditions heuristically determined by controller 110, coronal and/or sagittal plane leg loading, or any other such set of parameters. Many of these configurations would of course include feedback loop closure using stimulated musculature as physical actuators.

Note that a high-impedance state is indicated in waveform 701 during lateral stimulation, and that a high-impedance state is indicated in waveform 703 during medial stimulation. These high-impedance states disallow current flow through electrodes 204 and 205, respectively, of FIG. 2, preventing current flows through the leg that would otherwise (through current sharing) degrade stimulation specificity. Alternation of lateral and medial stimulation is shown at markers 719, 720, and 721, as lateral stimulation again occurs. During current sourcing to electrode 203 of FIG. 2 between markers 712 and 715, current sinking can be seen to electrode 207 of FIG. 2 until marker 713, and to electrode 208 of FIG. 2 until marker 714. Following FIG. 5 discussion above, it can be seen that higher pulsed direct current is therefore induced through the lateral portion of the joint than through the medial portion in this example. Note that this differential in direct currents forms as well a potential differential between lateral and medial portions of the joint.

It is assumed that the rate of current pulses applied to electrodes are of one or more frequencies to which muscle tissue may respond, such as between 20 to 5,000 Hz. It is also assumed that different frequencies may be applied to different muscle stimulation areas, so as to address factors such as penetration into a limb and specific muscle behaviors; and that differing frequencies may be applied to pulsed currents induced in or through joints. Embodiments are not limited to the biphasic muscle and monophasic joint stimulation shown. For example, an embodiment may utilize unipolar muscle and bipolar joint stimulation.

It is recognized that static joint loads may present situations wherein constant stimulation of one or more muscles may be advantageous, but that constant stimulation of a muscle attenuates blood flow through that muscle. Accordingly, an embodiment may incorporate maximum times for which a given muscle may be stimulated, and impose minimum rest times thereafter, before the maximum stimulation time is again allowed. In static load situations, therefore, muscle stimulation may become periodic at a slow rate, such as 0.3, 0.5, 1.0, 2.0 Hz and the like.

An embodiment addresses short-term adaptation made possible by stimulation which is in direct response to instantaneous conditions. This allows such an embodiment to adapt to changing physical conditions both proportionally and almost instantaneously.

Although many of the above embodiments address muscle stimulation of two areas, other embodiments may stimulate one, three or more areas. Furthermore, the differential stimulation disclosed above may be applied to not only balanced muscles or muscle groups, but to loosely-coupled muscles or muscle groups of a skeletal system, such as lower leg and back muscle groups.

Figure 8:
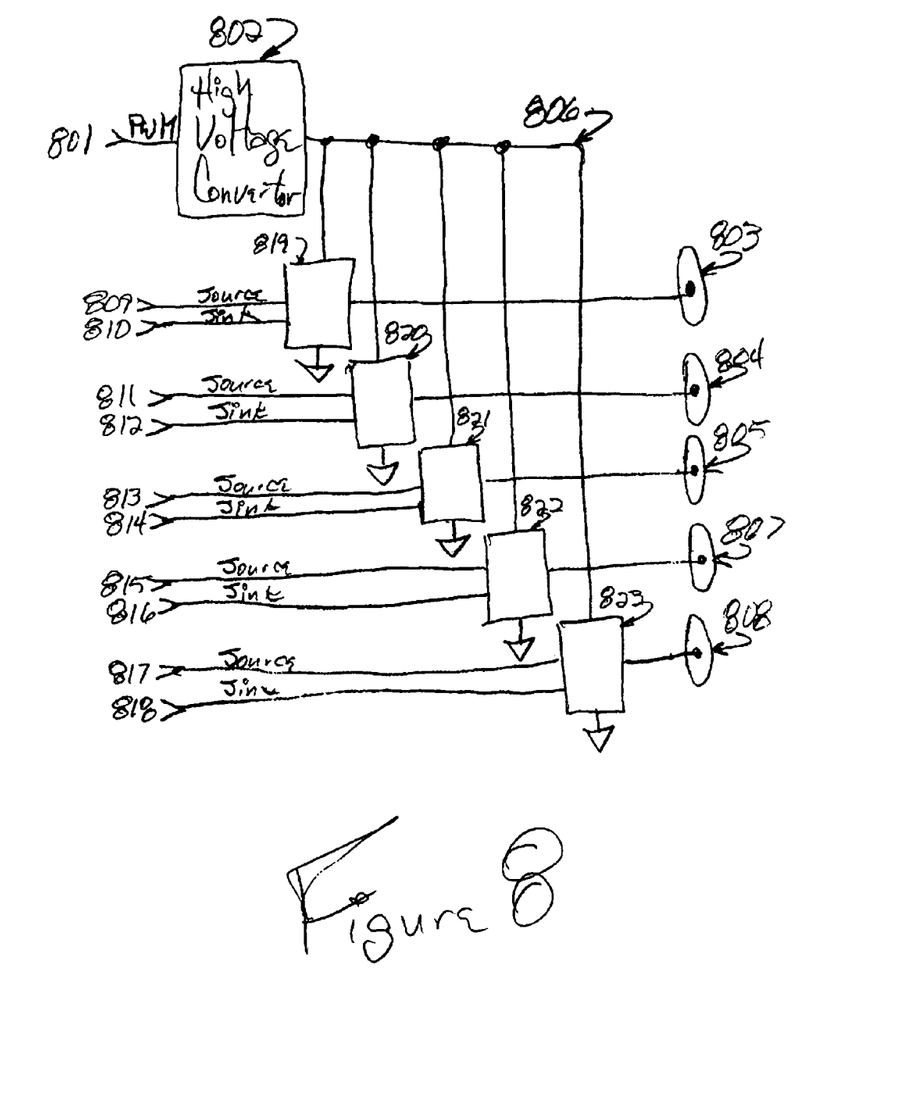
FIG. 8 includes a schematic circuit diagram for an embodiment of the invention.

FIG. 8 shows a block diagram of the stimulation output stage of an embodiment of the present invention. High voltage converter 802 receives as input PWM control signal 801, received from upstream control means within controller 110 of FIG. 1. Control signal 801 may be alternatively implemented with other pulse modulation techniques, such as pulse density modulation. In response to signal 801, converter 802 outputs high voltage 806, which is suitable for transcutaneous stimulation. High voltage 806 provides source voltage or current to switches 819, 820, 821, 822, and 823, which each receive source and sink control signals 809 and 810, 811 and 812, 813 and 814, 815 and 816, and 817 and 818, respectively, from upstream control means within controller 110 of FIG. 1. Switches 819, 820, 821, 822, and 823 each are capable of independent control over current sourcing and sinking. Such switches may include or be included in tri-state drivers. For example, tri-state logic or states allows a node to assume a high impedance state in addition to 0 and 1 logic levels or other analog levels. Converter 802 may provide a controlled current, in which case switches 819, 820, 821, 822, and 823 may be implemented as simple switches. Converter 802 may alternatively provide a controlled voltage, in which case switches 819, 820, 821, 822, and 823 may be implemented as controlled current switches.

In the event that switches 819, 820, 821, 822, and 823 are implemented as current switches, they may employ analog current control means, such as bipolar current limiters or JFETs; or pulse modulation means, such as pulse width modulation or pulse density modulation. Pulse modulation will result in improved efficiency over analog current control, so is anticipated for use in the present invention. In the event that current switches are used, it is assumed that specific output currents may be individually controlled by controller 110 of FIG. 1, such as through distribution of control signal 810 to each output switch.

Switches 819, 820, 821, 822, 823, and 824 each provide independently-controlled source and sink current to electrodes 803, 804, 805, 807, and 808, which correspond to electrodes 203, 204, 205, 207, and 208, respectively, all of FIG. 2.

Embodiments include independent voltage or current conversion stages for each electrode 803, 804, 805, 807, and 808 although other embodiments utilize a single conversion stage for economic reasons.

Thus, controller 110 of FIG. 1 is capable of independently-controlled source and sink current to be applied to electrodes 203, 204, 205, 207, and 208, all of FIG. 2.

By the discussion above, it can be seen that mechanical protection, possibly in concert with electrical encouragement for regeneration, may be accomplished without conflict or physical imbalance in various embodiments of the invention.

Figure 9:
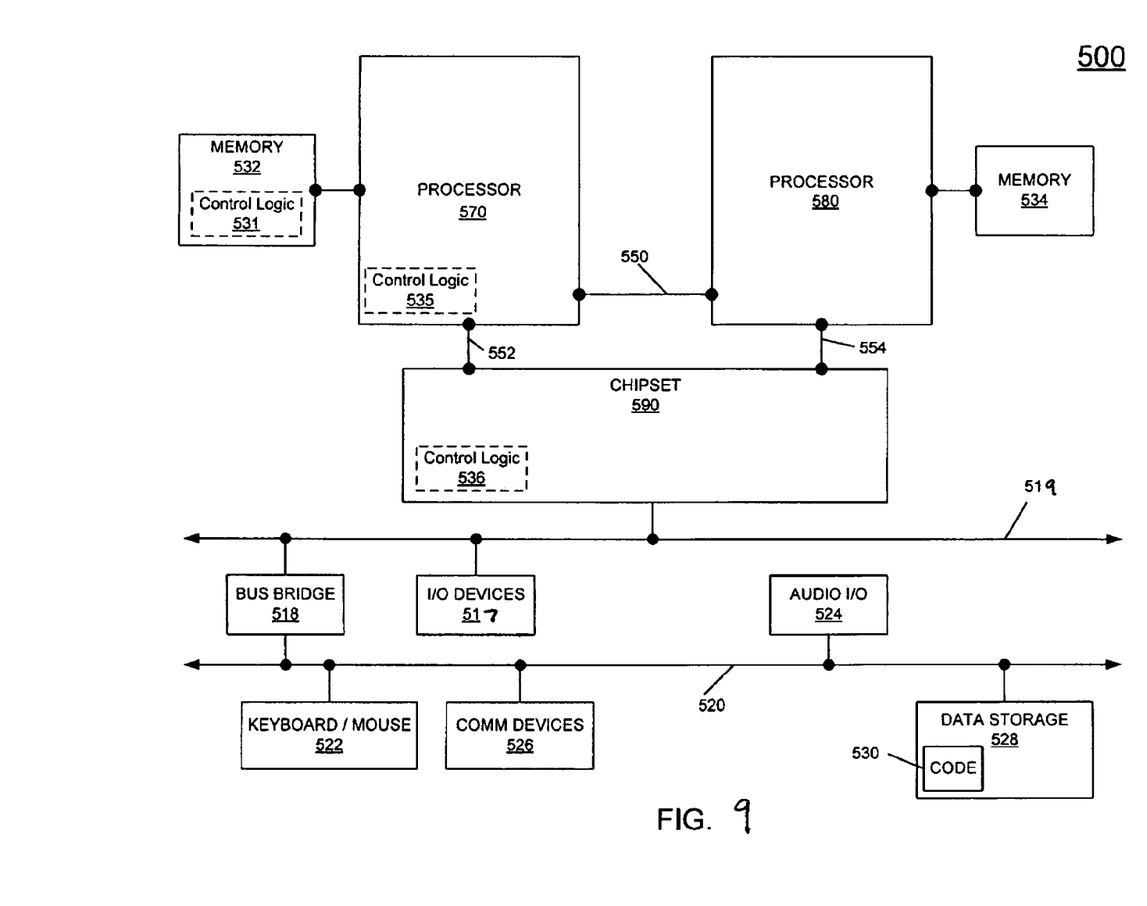
FIG. 9 includes a schematic diagram of a system for implementing various embodiments of the invention.

Embodiments may be implemented in many different system types. Referring now to FIG. 10, shown is a block diagram of a system in accordance with an embodiment of the present invention. Multiprocessor system 500 is a point-to-point interconnect system, and includes a first processor 570 and a second processor 580 coupled via a point-to-point interconnect 550. Each of processors 570 and 580 may be multi-core processors. The term "processor" may refer to any device or portion of a device that processes electronic data from registers and/or memory to transform that electronic data into other electronic data that may be stored in registers and/or memory. First processor 570 may include a memory controller hub (MCH) and point-to-point (P-P) interfaces. Similarly, second processor 580 may include a MCH and P-P interfaces. The MCHs may couple the processors to respective memories, namely memory 532 and memory 534, which may be portions of main memory (e.g., a dynamic random access memory (DRAM)) locally attached to the respective processors. First processor 570 and second processor 580 may be coupled to a chipset 590 via P-P interconnects, respectively. Chipset 590 may include P-P interfaces. Furthermore, chipset 590 may be coupled to a first bus 519 via an interface. Various input/output (I/O) devices 517 may be coupled to first bus 519, along with a bus bridge 518, which couples first bus 519 to a second bus 520. Various devices may be coupled to second bus 520 including, for example, a keyboard/mouse 522, communication devices 526, and data storage unit 528 such as a disk drive or other mass storage device, which may include code 530, in one embodiment. Code may be included in one or more memories including memory 528, 532, 534, memory coupled to system 500 via a network, and the like. Further, an audio I/O 524 may be coupled to second bus 520.

Embodiments may be implemented in code and may be stored on storage medium having stored thereon instructions which can be used to program a system to perform the instructions. The storage medium may include, but is not limited to, any type of disk including floppy disks, optical disks, solid state drives (SSDs), compact disk read-only memories (CD-ROMs), compact disk rewritables (CD-RWs), and magneto-optical disks, semiconductor devices such as read-only memories (ROMs), random access memories (RAMs) such as dynamic random access memories (DRAMs), static random access memories (SRAMs), erasable programmable read-only memories (EPROMs), flash memories, electrically erasable programmable read-only memories (EEPROMs), magnetic or optical cards, or any other type of media suitable for storing electronic instructions.

Embodiments of the invention may be described herein with reference to data such as instructions, functions, procedures, data structures, application programs, configuration settings, code, and the like. When the data is accessed by a machine, the machine may respond by performing tasks, defining abstract data types, establishing low-level hardware contexts, and/or performing other operations, as described in greater detail herein. The data may be stored in volatile and/or non-volatile data storage. The terms "code" or "program" cover a broad range of components and constructs, including applications, drivers, processes, routines, methods, modules, and subprograms and may refer to any collection of instructions which, when executed by a processing system, performs a desired operation or operations. In addition, alternative embodiments may include processes that use fewer than all of the disclosed operations, processes that use additional operations, processes that use the same operations in a different sequence, and processes in which the individual operations disclosed herein are combined, subdivided, or otherwise altered. In one embodiment, use of the term control logic includes hardware, such as transistors, registers, or other hardware, such as programmable logic devices (535). However, in another embodiment, logic also includes software or code (531). Such logic may be integrated with hardware, such as firmware or micro-code (536). A processor or controller may include control logic intended to represent any of a wide variety of control logic known in the art and, as such, may well be implemented as a microprocessor, a micro-controller, a field-programmable gate array (FPGA), application specific integrated circuit (ASIC), programmable logic device (PLD) and the like.

As used herein "simultaneously" may include overlapping portions. For example, two signals overlap if they start at the same instant in time, end at the same instant in time, or are both active at the same instant in time regardless of whether they start and/or end at the same instants in time.

Thus, in an embodiment a frame includes a portion including first and second electrode nodes (that couple to or include electrodes) to couple to tissue at a distance from a joint and an additional portion including first and second additional electrode nodes to couple to tissue at an additional distance from the joint. For example, the frame may be configured to extend across a knee or elbow joint with portion proximal to the joint and the additional portion distal to the joint. However, another embodiment may use a proximal center thigh electrode and two distal thigh electrodes just above the knee (i.e., the electrodes do not have to be on both sides of a joint to treat the joint).

The embodiment may include at least one processor, to couple to a memory and the frame, to perform operations comprising determining a first environmental condition, which corresponds to the joint, comprising at least one of force, location, and motion. For example the condition may be that the knee is moving, is experiencing loading, and/or is about to experience an increased load. The operations may comprise communicating first alternating current (AC) energy between the first and second electrodes to stimulate tissue located between the first and second electrodes based on the determined first environmental condition; and communicating first direct current (DC) energy between one of the first and second electrode nodes and one of the first and second additional electrode nodes based on the determined first environmental condition. Of course in other embodiments the DC may be communicate to one of the first and second additional electrode nodes from a node other then the first and second electrodes. For example, a third electrode located in the upper or proximal portion of the frame may deliver the DC current to either or both of the first and second additional electrodes.

An embodiment may include determining the first environmental condition for a portion of the joint (e.g., a medial portion or superior portion or inferior portion or later portion), and communicating the first AC energy to stimulate the tissue contralateral (e.g., lateral is contralateral to medial) to the portion based on the determined first environmental condition.

In embodiment increased force on the knee may call for increased AC energy to compensate and avoid pain. The increase in AC stimulus may be proportional to the increase in sensed force. However, the DC component is independent of the AC component and therefore the DC level may go unchanged. However, in other embodiments the DC component may change (greater or lesser energy) but may do so independently from the AC change.

In an embodiment a frame includes a portion including first and second electrode nodes to couple to tissue at a distance from a joint and an additional portion including a first additional electrode node to couple to tissue at an additional distance from the joint. Thus, in one embodiment three electrode nodes are used instead of the five of FIG. 2. Further, the electrodes may all be included close to one another. For example, the electrodes could be included in different portions of the upper strap of FIG. 2 or any other closely located portions of a frame. The embodiment may include at least one processor, to couple to a memory and the frame, to perform operations comprising (a) determining a first environmental condition, which corresponds to the joint, comprising at least one of force, location, and motion; (b) communicating first alternating current (AC) energy between the first and second electrodes to stimulate tissue located between the first and second electrodes based on the determined first environmental condition; and (c) communicating first direct current (DC) energy between one of the first and second electrode nodes and the first additional electrode node based on the determined first environmental condition.

An embodiment includes a method executed by at least one processor comprising: determining a first environmental condition, which corresponds to a joint, comprising at least one of force, location, and motion; communicating first alternating current (AC) energy between first and second electrodes to stimulate tissue located between the first and second electrodes based on the determined first environmental condition; and communicating first direct current (DC) energy between one of the first and second electrode nodes (or even another electrode node) and an additional electrode node based on the determined first environmental condition; wherein the first and second electrode nodes are included in a portion of a frame and couple to tissue a first distance from a joint and the first additional electrode node is included in an additional portion of the frame and couples to tissue an additional distance from the joint. Thus, the DC path may exist between electrodes (e.g. electrodes 3 and 4) other than those that communicate the AC energy (e.g., electrodes 1 and 2). Further, unipolar concepts may be used (such as DC energy emitted from a unipolar source).

While the present invention has been described with respect to a limited number of embodiments, those skilled in the art will appreciate numerous modifications and variations therefrom. It is intended that the appended claims cover all such modifications and variations as fall within the true spirit and scope of this present invention.

What is claimed is:

1. An apparatus comprising:
   a frame including an upper portion including first and second upper electrode nodes to couple to tissue on one side of a joint and a lower portion including first and second lower electrode nodes to couple to tissue on another side the joint;
   at least one processor, to couple to a memory and the frame, to perform operations comprising (a) determining an first environmental condition, which corresponds to the joint, comprising at least one of force, location, and motion; (b) communicating first alternating current (AC) energy between the first and second upper electrodes to stimulate tissue located between the first and second upper electrodes based on the determined first environmental condition; and (c) communicating first direct current (DC) energy between one of the first and second upper electrode nodes and one of the first and second lower electrode nodes based on the determined first environmental condition.

2. The apparatus of claim 1, wherein the upper portion of the frame includes a third upper electrode node and the at least one processor is to perform operations comprising conditioning a switching element corresponding to the third upper electrode node to induce a high impedance state for the third upper electrode node simultaneously with communicating the first AC energy between the first and second upper electrodes.

3. The apparatus of claim 1, wherein the at least one processor is to perform operations comprising communicating the first AC energy simultaneously with communicating the first DC energy.

4. The apparatus of claim 3, wherein the at least one processor is to perform operations comprising (a) determining the first environmental condition for one of medial and lateral portions of the joint, and (b) communicating the first AC energy to stimulate the tissue to decompress the one of medial and lateral portions based on the determined first environmental condition.

5. The apparatus of claim 3, wherein the at least one processor is to perform operations comprising (a) determining the first environmental condition for one of medial and lateral portions of the joint, and (b) communicating the first AC energy to stimulate the tissue contralateral to the one of medial and lateral portions based on the determined first environmental condition.

6. The apparatus of claim 5, wherein the at least one processor is to perform operations comprising communicating the first DC energy across the one of medial and lateral portions based on the determined first environmental condition.

7. The apparatus of claim 3, wherein the first AC energy has no DC energy component.

8. The apparatus of claim 3, wherein the at least one processor is to perform operations comprising (a) determining a second environmental condition, which corresponds to the joint and is unequal to the first environmental condition, comprising at least one of force, location, and motion; (b) communicating second AC energy between the first and second upper electrodes to stimulate tissue located between the first and second upper electrodes based on the determined second environmental condition; and (c) communicating second DC energy between the one of the first and second upper electrode nodes and the one of the first and second lower electrode nodes based on the second determined environmental condition;
wherein second AC energy is unequal to the first AC energy, the second DC energy is equal to the first DC energy, and communicated DC energy levels are independent of communicated AC energy levels.

9. The apparatus of claim 3, wherein the first environmental condition corresponds to a first force and the at least one processor is to perform operations comprising (a) determining a second environmental condition, which corresponds to a second force that is greater than the first force; (b) communicating second AC energy between the first and second upper electrodes based on the determined second environmental condition; and (c) communicating second DC energy between the one of the first and second upper electrode nodes and the one of the first and second lower electrode nodes based on the second determined environmental condition;
wherein second AC energy is greater than the first AC energy, the second DC energy is equal to the first DC energy, and the differential between the first and second AC energy levels is dependent on the differential between the first and second forces.

10. The apparatus of claim 3, wherein the at least one processor is to perform operations comprising sinking the first AC energy unequally between the first and second lower electrode nodes.

11. The apparatus of claim 1 comprising a first upper electrode to couple to the first upper electrode node; wherein one of the first upper electrode and the first upper electrode node includes a base and the other of the first upper electrode and the first upper electrode node includes a pivot member to be received by the base and pitch, roll, and yaw within the base.

12. The apparatus of claim 1, wherein the frame comprises:
an upper transverse member including the first and second upper electrode nodes and a lower transverse member including the first and second lower electrode nodes;
a coupling member to flexibly couple the upper transverse member to the lower transverse member;
wherein the coupling member is configured to support the upper transverse member above the lower transverse member but is not configured to support the body weight of a user of the frame.

13. A method executed by at least one processor comprising:
determining a first environmental condition, which corresponds to a joint, comprising at least one of force, location, and motion;
communicating first alternating current (AC) energy between first and second upper electrodes to stimulate tissue located between the first and second upper electrodes based on the determined first environmental condition; and
communicating first direct current (DC) energy between one of the first and second upper electrode nodes and one of first and second lower electrode nodes based on the determined first environmental condition;
wherein the first and second upper electrode nodes are included in an upper portion of a frame and couple to tissue on one side of a joint and the first and second lower electrode nodes are included in a lower portion of the frame and couple to tissue on another side of the joint.

14. The method of claim 13, wherein the upper portion of the frame includes a third upper electrode node and the method comprises conditioning a switching element corresponding to the third upper electrode node to induce a high impedance state for the third upper electrode node simultaneously with communicating the first AC energy between the first and second upper electrodes.

15. The method of claim 13 comprising communicating the first AC energy simultaneously with communicating the first DC energy.

16. The method of claim 13 comprising:
determining the first environmental condition for one of medial and lateral portions of the joint, and
communicating the first AC energy to stimulate the tissue contralateral to the one of medial and lateral portions based on the determined first environmental condition.

17. The method of claim 16 comprising communicating the first DC energy across the one of medial and lateral portions based on the determined first environmental condition.

18. The method of claim 13 comprising:
determining a second environmental condition, which corresponds to the joint and is unequal to the first environmental condition, comprising at least one of force, location, and motion;
communicating second AC energy between the first and second upper electrodes to stimulate tissue located between the first and second upper electrodes based on the determined second environmental condition; and
communicating second DC energy between the one of the first and second upper electrode nodes and the one of the first and second lower electrode nodes based on the second determined environmental condition;
wherein second AC energy is unequal to the first AC energy, the second DC energy is equal to the first DC energy, and communicated DC energy levels are independent of communicated AC energy levels.

* * * * *